US011964165B1

(12) United States Patent
Daffer (10) Patent No.: US 11,964,165 B1
(45) Date of Patent: Apr. 23, 2024

(54) CONTROLLABLE PHOTONIC CHAMBER (71) Applicant: Visibelle Derma Institute, Inc., Bloomington, MN (US)

(72) Inventor: Steven J. Daffer, Edina, MN (US)

(73) Assignee: VISIBELLE DERMA INSTITUTE, INC., Bloomington, MN (US)

( * ) Notice: Subject to any disclaimer, the term of this patent is extended or adjusted under 35 U.S.C. 154(b) by 538 days.

(21) Appl. No.: 16/824,090

(22) Filed: Mar. 19, 2020

Related U.S. Application Data (60) Provisional application No. 62/820,421, filed on Mar. 19, 2019.

(51) Int. Cl.
*A61N 5/06* (2006.01)

(52) U.S. Cl.
CPC .... *A61N 5/0625* (2013.01); *A61N 2005/0626* (2013.01); *A61N 2005/0638* (2013.01); *A61N 2005/066* (2013.01); *A61N 2005/0662* (2013.01); *A61N 2005/0666* (2013.01)

(58) Field of Classification Search
CPC .......... A61N 5/0625; A61N 2005/0626; A61N 2005/0638; A61N 2005/066; A61N 2005/0662; A61N 2005/0666
USPC .......................................................... 607/100
See application file for complete search history.

(56) References Cited

U.S. PATENT DOCUMENTS

| | | | |
|---|---|---|---|
| 4,546,236 A | 10/1985 | Janson | |
| 5,255,399 A | 10/1993 | Park | |
| D341,425 S | 11/1993 | Lee | |
| 6,745,411 B1 | 6/2004 | Kjonaas | |
| 9,629,777 B2 | 4/2017 | Shurtleff | |
| D859,674 S | 9/2019 | Smith | |
| 2004/0030371 A1* | 2/2004 | Barghelame | A61H 33/06 607/96 |
| 2006/0059618 A1 | 3/2006 | Chung et al. | |
| 2006/0229691 A1* | 10/2006 | Noskov | A61F 7/0053 607/96 |

(Continued)

FOREIGN PATENT DOCUMENTS

EP 1593914 A2 11/2005
KR 100581764 B1 12/2005

OTHER PUBLICATIONS

"Which sauna doors are the best to choose, Aug. 31, 2018, eSauna Shop, https://esaunashop.com/which-sauna-doors-are-the-best-to-choose" (Year: 2018).*

(Continued)

*Primary Examiner* — Joseph M Dietrich
*Assistant Examiner* — Michael T. Holtzclaw
(74) *Attorney, Agent, or Firm* — Peter J. Ims; Westman, Champlin & Koehler, P.A.

(57) ABSTRACT

A chamber providing controlled amounts and wavelengths of photonic IR and visible light within an internal space sized for at least one human being to exercise therein. The chamber includes at least one emitter system configured to emit FIR energy and at least one emitter system configured to emit at least MIR energy. The chamber includes at least one light emitting source configured to emit full spectrum visible light and/or a selected wavelength of visible light, and a control panel configured to control the amount, wavelengths and duration of FIR, MIR, and visible light within the chamber.

21 Claims, 8 Drawing Sheets

(56) References Cited

U.S. PATENT DOCUMENTS

| | | | |
|---|---|---|---|
| 2007/0050903 A1* | 3/2007 | Sappenfield | A61H 33/06 |
| | | | 4/524 |
| 2007/0235439 A1 | 10/2007 | Chen | |
| 2007/0294819 A1 | 12/2007 | Levesque | |
| 2008/0196152 A1* | 8/2008 | Lozano | A61H 33/066 |
| | | | 4/527 |
| 2009/0126098 A1 | 5/2009 | Gong | |
| 2010/0017953 A1* | 1/2010 | O'Keeffe | A61H 33/06 |
| | | | 219/480 |
| 2013/0042402 A1 | 2/2013 | Parker | |
| 2014/0157511 A1 | 6/2014 | Shurtleff | |
| 2014/0209594 A1 | 7/2014 | Besner | |
| 2015/0127076 A1 | 5/2015 | Johnson et al. | |
| 2016/0310776 A1 | 10/2016 | Smith | |
| 2017/0056718 A1 | 3/2017 | Davis | |
| 2017/0367929 A1* | 12/2017 | Durfee | A61N 5/0625 |
| 2020/0008996 A1* | 1/2020 | Zack | A61H 33/14 |
| 2020/0398078 A1 | 12/2020 | Jensen | |

OTHER PUBLICATIONS

Https://www.covewellness.com/jade-infrared-saunas/ (Year: 2017).

* cited by examiner

CONTROLLABLE PHOTONIC CHAMBER

CROSS-REFERENCE TO RELATED APPLICATION

This application is based on and claims the benefit of U.S. provisional application Ser. No. 62/820,421, filed Mar. 19, 2019, the content of which is hereby incorporated in its entirety.

BACKGROUND

The present disclosure relates to a chamber in which the amount, time and type of beneficial photonic energy delivered to a person is controlled within a chamber. In particular, the present disclosure includes a chamber that provides selected wavelengths and dosages of infrared and visible light that are beneficial to a human being while eliminating photonic energy that is damaging to at least the skin of the human being.

Many people seek the benefits of the sun for the health benefits that the visible and infrared spectrum provides to the human body. These benefits include warmth from the IR spectrum and certain wavelengths that provide healing, aesthetic enhancements and wellness to the body. However, the sun's electromagnetic spectrum includes the complete IR spectrum, visible light spectrum and the ultraviolet spectrum. The ultraviolet spectrum can damage the skin and can cause adverse skin lesions and cancer, aging and wrinkles.

Many people also use saunas to provide thermal benefits to the body. However, typical saunas use heat or infrared sources that do not utilize controllable wavelengths. For instance, when heated bodies, such as hot rocks are utilized, the typical way to control the temperature in the sauna is to add or remove heated bodies, which can lead to temperatures that exceed the upper limit of hyperthermic benefits to the body or are below the lower end of the range of temperatures that provide hyperthermic benefits to the body.

Some people utilize dry saunas that utilize heat generated by heaters that produce far infrared (FIR) energy. FIR energy is typically defined as radiation with a wavelength of 15,000 nm to about 100,000 nm (corresponding to a range of about 20 THz to 300 GHz). However, while heating a person's body, FIR energy does not provide a quick sensation of heating the body.

SUMMARY

An aspect of the present disclosure relates to a chamber the provides controlled dosages and amounts and selected wavelengths of IR and visible light within an internal size to allow one or more people to perform isotonic or dynamic exercise. The chamber includes at least one emitter system configured to emit far-infrared (FIR) energy and at least one emitter system configured to emit at least mid-infrared (MIR) energy. The chamber includes at least one light emitting source configured to emit selected and/or all wavelengths of visible light, and a control panel configured to control the amount, wavelengths and duration of FIR, MIR and visible light within the chamber.

In some aspects, synthetic and/or natural stones and/or crystals are placed within the internal space, where the natural stone emit FIR photons when heated. Exemplary natural stones and/or crystals include, but are not limited to, jade, tourmaline, amethyst, sapphire and quartz. In some instances, the natural stones are placed directly in front of IR heaters, which aid in the emission of FIR from the natural stones. In some instances, the heat within the chamber is used to heat the natural stones to cause FIR photons to be emitted.

In some aspects, visible wavelength light can be utilized with the multispectrum IR photonic energy. For instance, by non-limiting example, red light having a 640 nm wavelength can be utilized within the chamber along with the multispectrum IR photonic energy.

In other aspects, the chamber can include blocks of salt, such as natural mineral salt, that when heated emit infrared wavelengths and/or ions that cleanse the air.

In some aspects, a control panel is configured to control the amount, selected wavelengths and duration of FIR, MIR, and visible light within the chamber wherein the chamber is sized to allow one or more person to perform isotonic or dynamic exercises. The overall environment within the chamber is selectively controllable including a temperature, wavelength of visible light, oxygen content, moisture content, infusion of carbon-based materials, visual effects, sound effects, aromas, and combinations thereof.

Another aspect of the present disclosure relates to a method of customizing an environment within in a chamber for one or more person to exercise. Customize the environment includes selecting a wavelength and duration of FIR energy, MIR energy and visible light within the chamber. Panels comprising natural stones capable of absorbing IR energy are removably installed in front of at least one emitting system configured to emit FIR energy. Natural salt blocks capable of absorbing IR energy also further customize the environment in addition to selection of temperature, oxygen content, moisture content, visual effect, sound effect, aroma, or combinations thereof within the chamber.

DETAILED DESCRIPTION

The present disclosure is directed to a photonic chamber having an internal space that is of a sufficient size to comfortably sit one or more people or to allow one or more people to move, stretch, stand and/or perform active exercises. The environment within the chamber can be individually selected and controlled depending on the one or more user's preferences.

The chamber includes a plurality of IR heaters that output photons in the mid infrared spectrum (MIR) and the far infrared spectrum (FIR). The MIR has a range of wavelengths from about 1,500 nm to about 5,600 nm. The FIR has a range of wavelengths from about 5,600 nm to about 100,000 nm. Utilizing the plurality of IR heaters that emit photons in the MIR and FIR frequencies, the person experiences the benefits of each spectrum of frequencies. For instance, the MIR provides for total body heating while the FIR provides deep heating to the person's body. Therefore, over time the person experiences the medium and deeper photonic experiences of the MIR and FIR.

The chamber also has full spectrum visible light and visible light energy in selected wavelengths. The environment in the chamber can also provide halotherapy and aromatherapy. The chamber is configurable and customizable to allow one or more people to exercise within a selected custom environment within the chamber, which provides enhanced physical benefits relative to exercising, active recovery, active rest and/or passive relaxation in ambient conditions. At least the MIR, and/or FIR heaters, panels of natural stones, and panels of visible light are removable and selectively configurable between uses such that a user can select a personalized ambiance and/or customized photonic environment that provides the beneficial IR photonic energy and the beneficial visible light photonic energy, while eliminating the photonic energy that is harmful to a person's body, such as ultraviolet light and photonic wavelengths that are shorter or longer than the visible and infrared spectrums.

Figure 1:
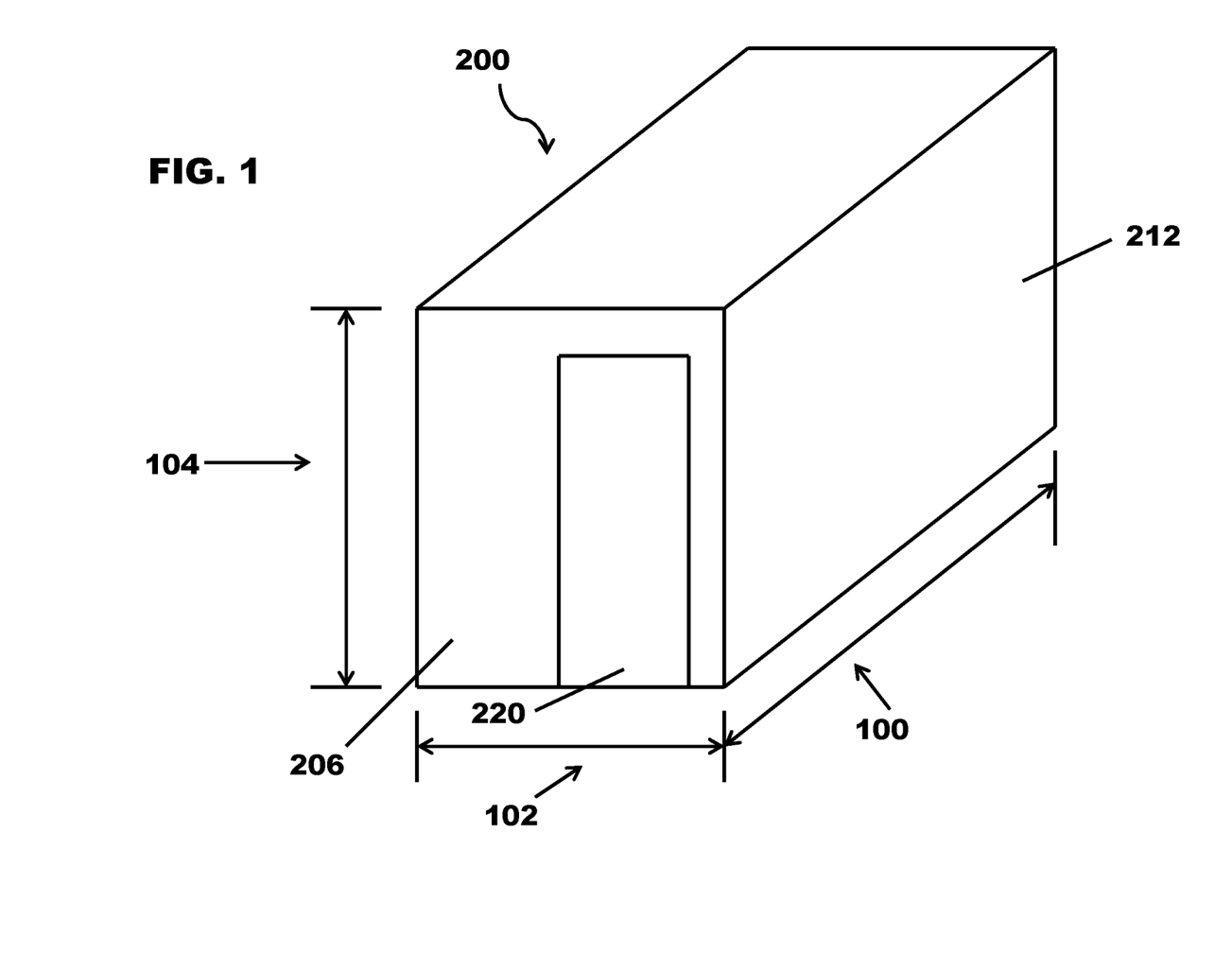
FIG. 1 is a perspective exterior view of a customizable controllable photonic chamber.

The photonic chamber configured to allow one or more people to exercise is illustrated at 200 in FIGS. 1-8. As illustrated in FIG. 1, the assembled photonic chamber 200 has a length 100 ranging from about 7 feet to about 11 feet, a width 102 ranging from about 5 feet and about 9 feet and a height 104 ranging from about 7 feet and about 10 feet. The dimensions of the chamber 200 allow the chamber 200 to be assembled inside any typically sized room. Further, the chamber 200 is provided with one or more plug-in 232 for connection to any standard 110 volt AC socket for powering the components in the chamber 200.

As illustrated in FIG. 2-8, the photonic chamber includes a floor 202, a ceiling 204, a front wall 206, a back wall 208, a left side wall 210 and a right side wall 212. Each wall 206, 208, 210 and 212 is connected together at vertical ends that form corners. Each wall 206, 208, 210 and 212 is also connected to the floor 202 and the ceiling 204 to form the chamber 210 that allows the environment therein to be controlled. Each wall 206, 208, 210, 212 and floor 202 and ceiling 204 may be constructed of one or more panels or sections. In the embodiment illustrated each of the floor 202, ceiling 204, front wall 206, back wall 208, left side wall 210 and right side wall 212 are constructed from two panels. The panels are connected along their length which allows for easy assembly and transport or shipping with a reduction in costs.

The chamber 200 may be transported or shipped as a kit for on-site installation comprising panels which form each of the floor 202, ceiling 204 and walls 206, 208, 210, 212. Exemplary environmental conditions that can be controlled within the assembled chamber 200 include, but are not limited to, doses of FIR, MIR and duration thereof, temperature, the wavelength of visible light, oxygen content, moisture content, infusion of carbon-based materials, visual effects, sound effects, aromas, and combinations thereof. As such, the environment can be customized for any exercise routine and/or fitness level of a person or persons utilizing the photonic chamber 200.

Figure 2:
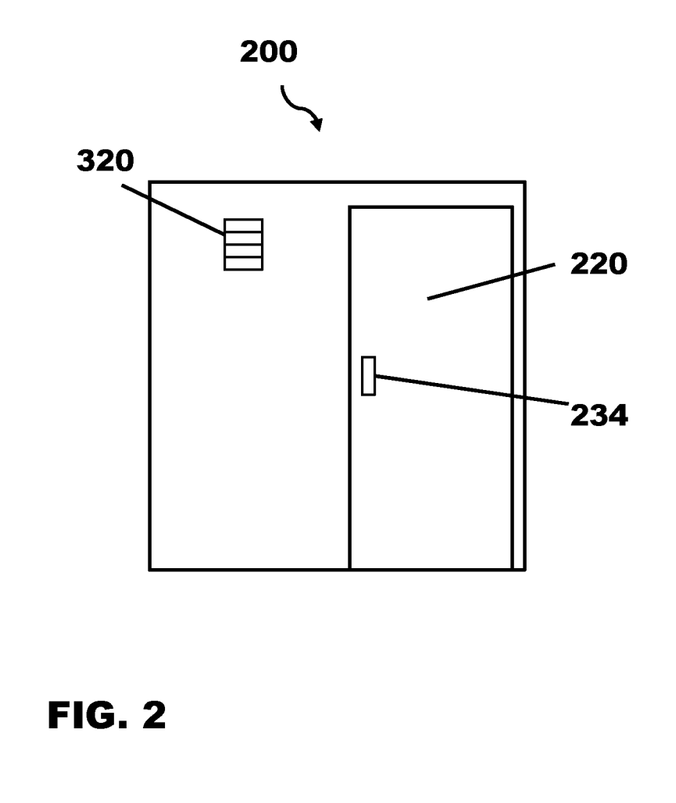
FIG. 2 is a plan view of a front exterior wall.
Figure 3:
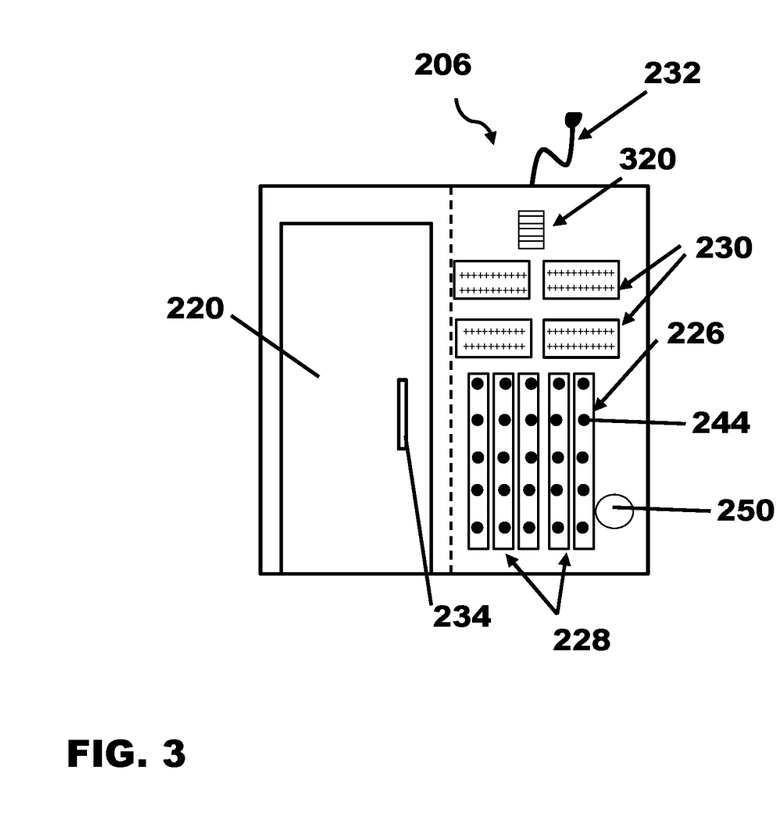
FIG. 3 is a plan view of a front interior wall of the controllable photonic chamber.

Referring to FIGS. 2-3, one wall, referred to herein as the front wall 206, includes a door 220 to provide access to the interior of the chamber 200. In an exemplary embodiment, the door 220 is a sliding glass door. However, a hinged door is also within the scope of the present disclosure. The door 220 may include a handle 234 on an outside surface of the door 220 and an inside surface of the door 220, where the handle 234 is typically constructed of a material that does not readily conduct heat, such as wood, to prevent the handle from becoming hot to the touch when the internal space of the chamber 200 is heated.

The interior front wall 206 or another wall 208, 210, 212 of the chamber 200 may also be provided with a window (not illustrated). The door 220 and window may be frosted, coated, or otherwise provided with a texture on one or both of the interior and exterior surfaces. The frosting, coating, and/or texture is a coating or texture applied to the door 220 and window which reflects photons emitted within the chamber 200 to prevent photon loss through the door 220 or window and thus maintain the selected environment within the chamber 200. In an alternative embodiment, the door 220 is optically transparent or translucent to allow a person outside of the chamber 200 to monitor activity within the chamber 200. While the door 220 allows a person to monitor or detect the activity within the chamber 200, the door 220 also provides a sufficient seal to maintain the desired environmental conditions within the chamber 200 such as temperature or aromatherapy. An enriched air intake fan 250 is also provided to the chamber, and as illustrated is provided in the front wall 206.

Referring to FIG. 3, the interior front wall 206 includes a plurality of FIR heaters 228 that are typically carbon fiber and a plurality of MIR heaters 230, which are typically ceramic. As illustrated the plurality of FIR heaters 228 are located below the plurality of MIR heaters 230. However, the arrangement and location of the plurality of FIR heaters 228 and MIR heaters 230 is exemplary and can be in any suitable configuration and number with the FIR heaters 228 being the same or different sizes. The configuration of the FIR heaters 228 is further customizable. As previously mentioned, the FIR heaters 228 emit photons that provide deeper penetration of the skin that does not provide the immediate sensation of heat. However, over time, the body can feel the energy imparted into the body from the FIR heaters 228 in the form of heat.

The FIR heaters 228 are generally located behind a panel 226 configured to receive a plurality of natural stones 244. An exemplary natural stone 244 is jade, however any suitable natural stone could be utilized. The panels 226 are configured for removable insertion panels with different natural stones to allow users to further customize the environment within the chamber 200.

Figure 4:
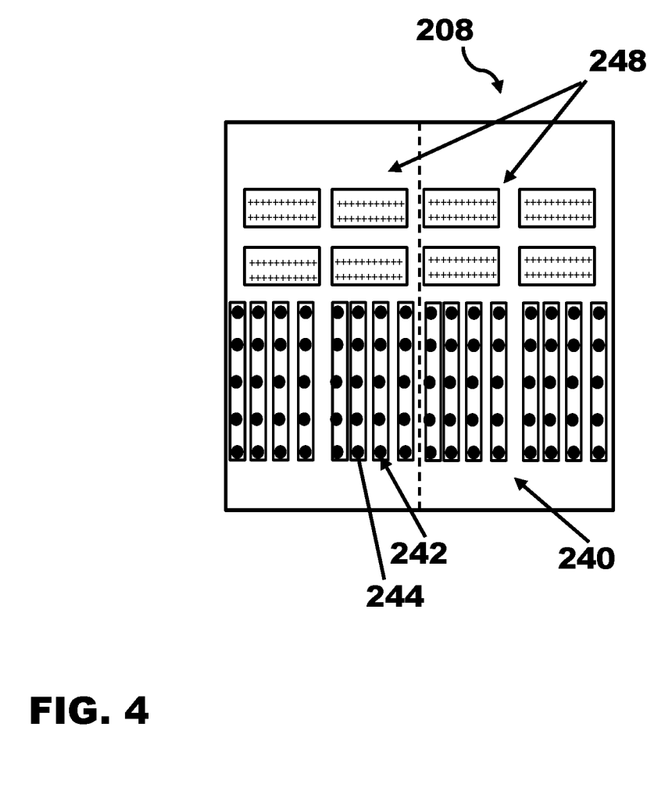
FIG. 4 is a plan view of a back interior wall of the controllable photonic chamber.

As illustrated in FIG. 4, the interior back wall 208 is substantially the same size and parallel to the front wall 206. The back wall 208 includes a plurality of FIR heaters 240 that are typically carbon fiber and a plurality of MIR heaters 248, which are typically ceramic. As illustrated the plurality of FIR heaters 246 are located below the plurality of MIR heaters 248. However, the arrangement and location of the plurality of FIR heaters 246 and MIR heaters 248 is exemplary and can be in any suitable configuration and number. The plurality of FIR heaters 240 are each located behind a panel 242 containing a plurality of natural stones 244, where an exemplary and non-limiting example of the natural stone 244 is jade.

Figure 5:
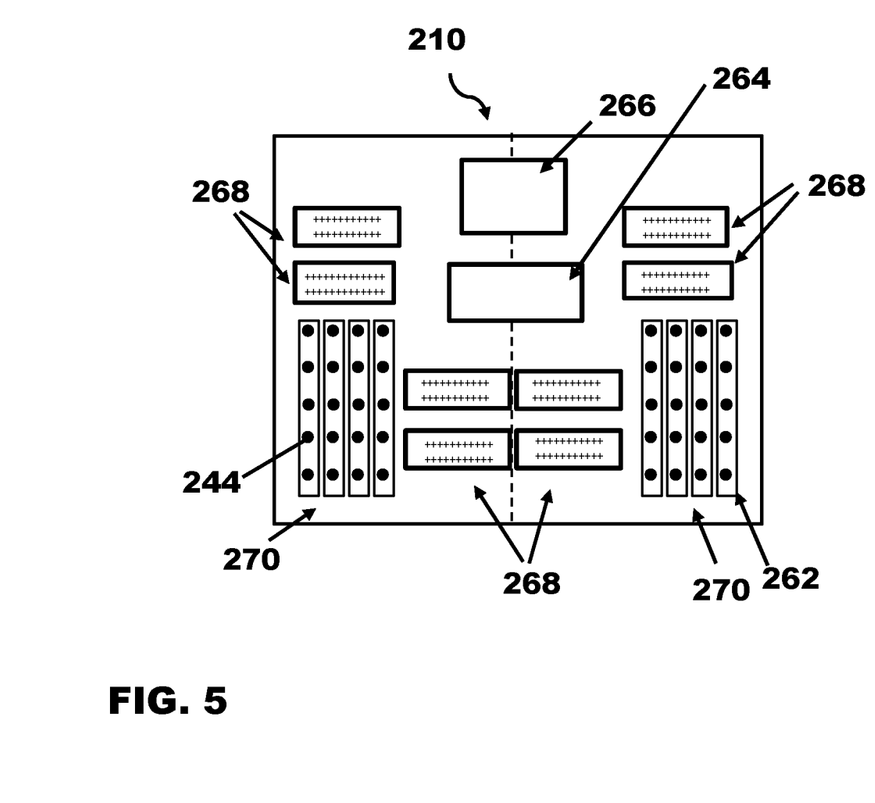
FIG. 5 is a plan view of a side interior wall of the controllable photonic chamber.

As illustrated in FIG. 5, the left side wall 210 includes a plurality of FIR heaters 270 that are typically carbon fiber and a plurality of MIR heaters 268, which are typically ceramic. As illustrated the plurality of MIR heaters 268 are located above and between the plurality of FIR heaters 270. However, the arrangement and location of the plurality of FIR heaters 270 and MIR heaters 268 is exemplary and can be in any suitable configuration and number. Each FIR heater 270 is located behind a panel 262 containing a plurality of natural stones 244, where an exemplary and non-limiting example of the natural stone is jade. As illustrated, the lower MIR heaters 268 are arranged such that the side wall 210 provides sufficient space to mount or support a screen 266 and signage 264. However, a panel with natural stones is not required in front of any one or all of the FIR heaters and such panels may be optionally placed in front of the FIR heaters for customization of the chamber 200 environment.

Figure 6:
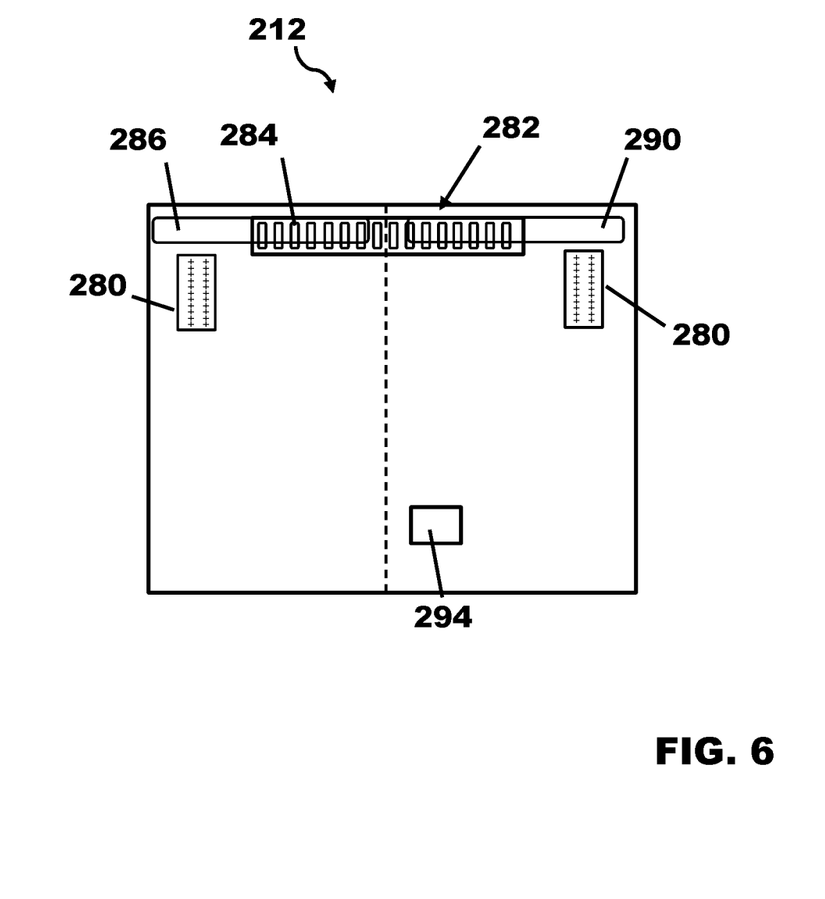
FIG. 6 is a plan view of another side interior wall of the controllable photonic chamber.

As illustrated in FIG. 6, the right side wall 212 includes a plurality of IR heaters 280 located near a plurality of salt panels 282. An exemplary salt panel 282 includes, but is not limited to, cavities configured to receive Himalayan salt panels, salt bricks or salt blocks that include a plurality of trace minerals. The salt panel may also be a heated salt panel 282 to emit infrared energy and ions that provide halo-therapy to the user. The salt panel 282 may feature a row of a plurality of salt blocks or salt bricks 284, which may further be backlit to customize the environment in the chamber 200. For example, the salt panel 282 may be backlit with orange or red light. In the embodiment illustrated, the back wall includes cavities for holding up to sixteen (16) salt bricks in addition to one or more heaters such as ceramic heaters.

The right side wall 212 is generally open along a lower section of the wall 212 to allow users within the chamber 200 to contact the side wall 212 during one or more exercises. For example, the IR heaters and salt panels are positioned near a top portion of the right side wall 212 leaving the mid and lower portion of the wall exposed. Users in the chamber may lean against the wall or otherwise use the wall for bracing or resistance during exercise within the chamber 200.

The right side wall 212 may also be provided with an access door 294 such as a sliding door for access to one or more electrical sockets for electrical connection of optional equipment brought into the chamber 200.

Any one or more of the walls may be provided with a plurality of LED arrays typically configured to emit red light at about 640 nm. In the embodiment illustrated, the right side wall 212 includes a left plurality of LED arrays 286 proximate an upper left corner of the right side wall 212 and a right plurality of LED arrays 290 proximate an upper right corner. The LED arrays 286 and 290 typically are configured to emit red light at about 640 nm. However, the LED arrays 286 and 290 can be controlled to emit the full spectrum of visible light or any wavelength rage including each of the individual colors, a plurality of colors up to and including full spectrum, white light.

Figure 7:
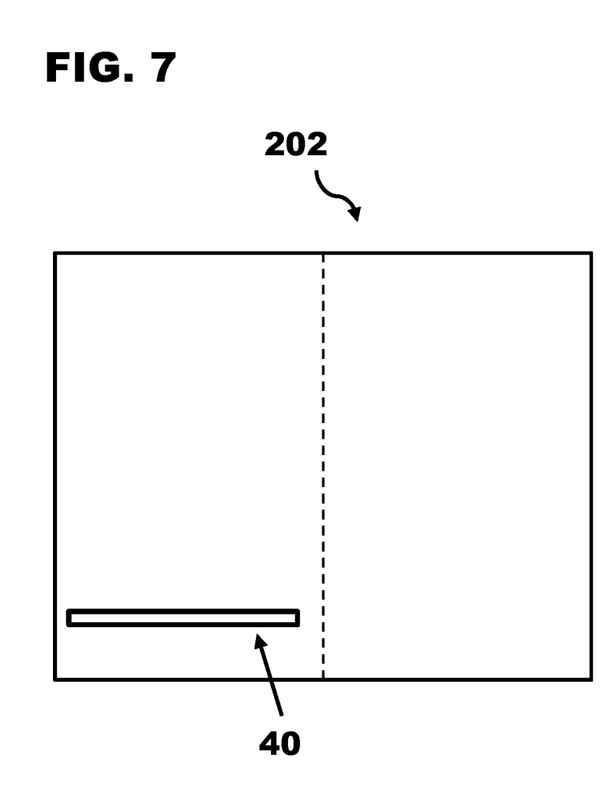
FIG. 7 is a plan view of a floor of the controllable photonic chamber.

As the photonic chamber 200 can be utilized for exercising, the floor 202 illustrated in FIG. 7 is substantially flat to allow the user(s) to be able to move within the chamber 200 without any tripping hazards on the floor 202. The floor 202 is typically constructed of a material that does not cause injury due to repetitive movement. An exemplary, but non-limiting, material of construction of the floor 202 includes wood. It is also contemplated that in one or more embodiments, wooden benches may also be provided for positioning along the walls and/or in corners to provide perimeter seating at one or more locations within the chamber 200.

Figure 8:
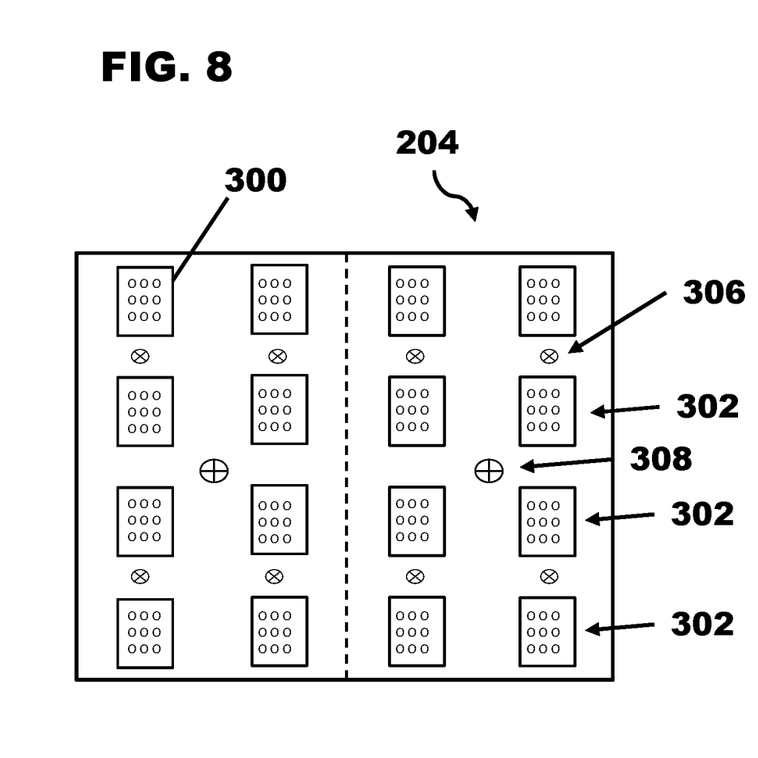
FIG. 8 is a plan view of a ceiling of the controllable photonic chamber.

The ceiling 204 is illustrated in FIG. 8 and includes a plurality of spaced apart LED arrays 300. The plurality of LED arrays 300 are arranged in rows 302 of spaced apart arrays to provide substantially uniform distribution of the emitted light throughout the chamber 200. The plurality LED arrays 300 typically are configured to emit red light at about 640 nm. However, the LED arrays 300 can be controlled to emit any wavelength range including each of the individual colors, a plurality of colors up to and including full spectrum, white light.

The ceiling 204 is further provided with ceiling lights 306 for selected uses and speakers 308 which are operably connected to the display and sound system for further controlling the audial environment in the chamber 200.

Each array 286, 290, 300 includes a plurality of LEDs that can emit red light having 640 nm wavelengths. The arrays 286, 290, 300 of red chromo-light modules provide for ATP stimulation, enhanced energy, fitness or workout recovery, serene ambiance and illumination. While the position of the LED arrays has been described above with respect to locations on each wall, any number of arrays with any number of lights emitting the visible light spectrum or a selected wavelength within the visible spectrum is within the scope of the present disclosure.

In one or more embodiments, the chamber 200 includes a seat 40 that may extend along one or more walls 206, 208, 210 or 212 where the seat 40 has a length that is configured to comfortably allow one or more people to sit in the internal space of the chamber 210. In such embodiments, the plurality of IR heaters is strategically located about the seat 40 to provide the NIR, MIR and FIR frequencies therearound.

The FIR/MIR heaters described herein can be any suitable heater that emits FIR/MIR wavelength energy including, but not limited to, a ceramic heater or a carbon fiber heater. In one embodiment, the FIR heaters may be carbon fiber heaters that emit FIR photons. However, any suitable heater that emits FIR/MIR wavelength energy including, but not limited to, a ceramic heater can be utilized.

While the MIR and FIR heaters are described herein being in a particular location and emitting a particular spectrum of wavelengths, the present disclosure is not limited to the specific configuration of heaters. Rather, any number of MIR and FIR heaters can be utilized provided that the substantially full spectrum of IR energy is emitted within the internal cavity of the chamber 200.

As described above, the FIR heaters on any one or more of the walls 206, 208, 210, 212 may be covered by panels 226, 242, 262 that are removable and that are similarly constructed to retain natural stones therein such that, when heated, the stones emit desired IR energy. Where FIR photons are emitted from the FIR heaters, at least some FIR photons are allowed to pass into the chamber 200 while at least some FIR photons engage the natural stones selectively installed in front of the FIR heaters thus emitting desired IR energy from the stones.

The panels 226, 242, 262 are removable and customizable in that the panels 226, 242, 262 can hold stones of one or more types and the panels 226, 242, 262 may cover any or all of the respective FIR heaters. A user can select the same or combinations of different natural stones to populate the panels 226, 242, 262 to provide a desired emitted IR frequency. By way of non-limiting example, the panels 226, 242, 262 with jade stones can be slidably removed from connective brackets or otherwise disengaged from connection with the respective interior wall and replaced with panels containing quartz or tourmaline, or combinations thereof.

In another embodiment, panels of natural stones may be secured to corresponding fasteners on one or more walls of the chamber 200 or otherwise installed in the chamber in a manner where the natural stones are not in front of a FIR heater. In such embodiments, the stones rely on absorbing the heat generated in the chamber for activation.

As described above, the chamber 200 includes one or more cavities for holding mineral salt blocks, such as Himalayan salt blocks to provide for halotherapy within the chamber 200. When heated, the minerals in the salt blocks emit infrared wavelengths and/or ions that cleanse the air and when inhaled can also provide beneficial health effects.

Figure 9:
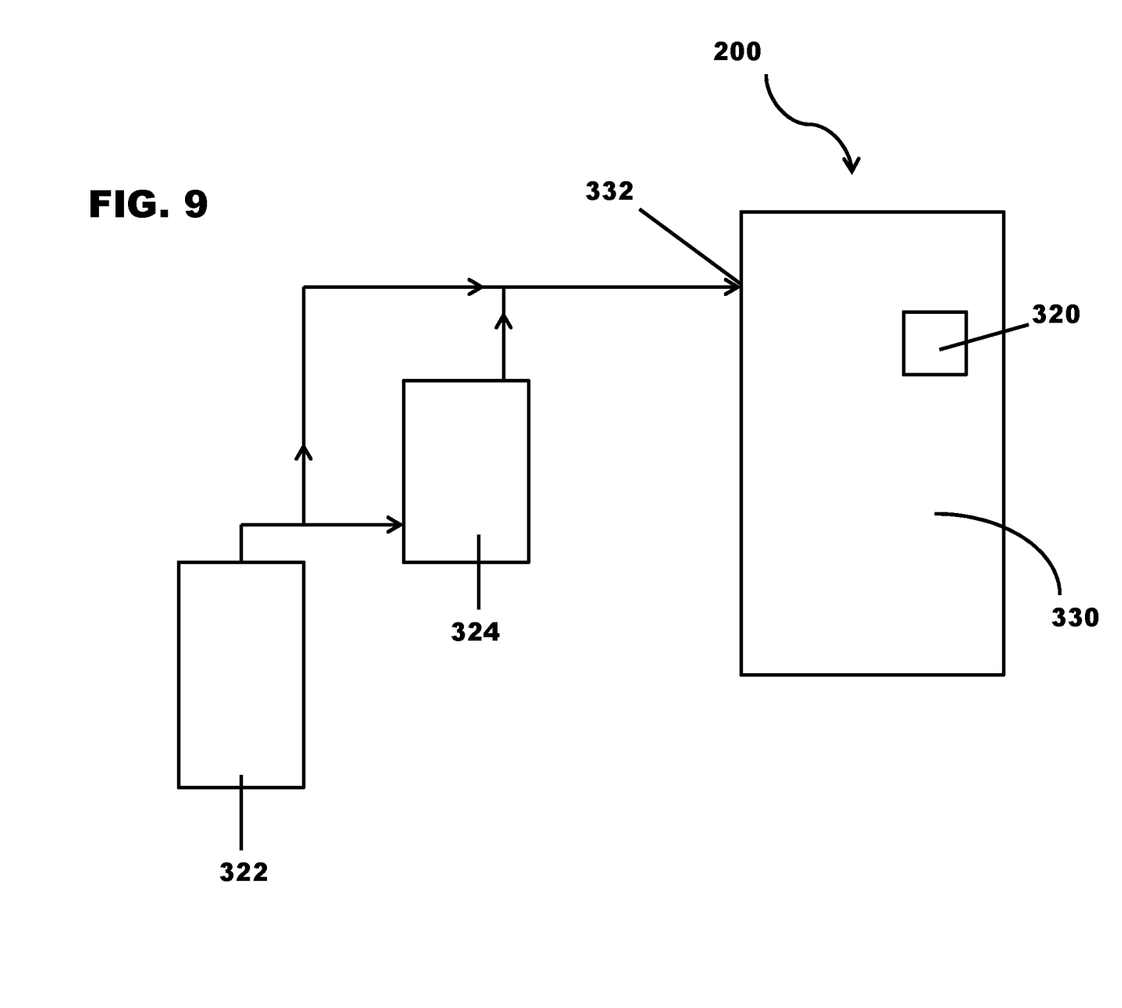
FIG. 9 is a schematic view of a system for controlling the ambient environment within the chamber.

Referring to FIG. 9, a schematic of the chamber 200 with a control panel 320 and one or more optional and external environmental changing devices 322 and 324 are illustrated. The control panel 320 is illustrated being located on an outer surface 330 of the chamber 200. However, the control panel 320 can be located within the chamber 200 or two control panels 320 can be utilized, with one exterior to the chamber 200 and one within the chamber 200.

The environmental changing device 322 is configured to generate air with enriched oxygen which is forced into an opening 332 within the chamber to increase the oxygen content within the chamber 200. The environmental changing device 324 is configured to provide moisture or humidity to the chamber. In one embodiment, the oxygen enriched air is forced through a pool of water, typically distilled water, to increase and control moisture content within the chamber 200.

In some optional embodiments, the liquid can be infused with essential oils to provide aromatherapy. In alternative optional embodiments, additional carbon-based compounds can be added to the liquid to provide other desired effects. The additional carbon-based compounds include, vitamins, aloe vera, caffeine and the like.

As mentioned above, the chamber according to embodiments described herein is configured to be used by one or more people to exercise. The exercises can be isotonic or dynamic in nature. The exercises include resistance training such as with weights or resistance bands, using stationary exercise devices such as treadmills, elliptical machines, stationary cycles and rowing machines, various types and disciplines of yoga, tai chi, active recovery, active rest disciplines, stretching, assisted stretching, assisted massage, physical therapy manipulation and combinations thereof.

The control panel 320 can be utilized to control the temperature, type of visible light utilized, such as red light in about the 640 nm wavelength or full spectrum light in the range between about 400 nm to about 720 nm, and the environment within the chamber 200, such as by controlling oxygen concentration and humidity. Additionally, the control panel 320 can be utilized to power the screen 266. The screen 266 can be utilized to play a pre-recorded exercise routine, a natural scene such as the stars in a night sky or any other visible image that is desired.

The screen 266 can have speakers or can be wired or wirelessly connected with speakers within the chamber 200. Alternatively, the screen 266 can be wirelessly connected to a user's headphones. In some embodiments, the screen 266 can be Wi-Fi enabled such that the user can place desired audio/visual content on the screen 266 from a cell phone or other electronic device.

Utilizing the combination of the full spectrum IR heat, visible light and modified environment provides numerous physical and psychological advantages over other forms of exercise. For instance, exercising in heat typically increases core body temperature, increases heart rate, increases perspiration and activates heat shock proteins such as HGH for muscles, and other mind and body biochemistry outputs for improved neuro health, such as HGH for much.

A result of heat training improves a person's ability to cool oneself. Further, the benefits of exercising in heat provides benefits that exceed altitude training, produces quicker improvements in fitness, increases lactate threshold which increases cardiovascular capacity and ability to do intense work for longer periods of time. Additionally, exercising in heat increase a person's psychological tolerance for tough workouts.

Along with the benefits of training in heat where the body engages a full spectrum of IR photons, the presently disclosed chamber 200 provides light in the red light spectrum ranging from about 630 to about 670 nm and IR about 730 and about 950 nm. Subjecting the body to red light provides photobiomodulation. The benefits of this exposure include improved skin health, reduced joint pain, enhanced muscle recovery and weight loss.

Additionally, photobiomodulation affects the mitochondria in cells. The mitochondria produces adenosine triphosphate (ATP) which is produced through cellular respiration. While not being bound to theory, it is believed that photobiomodulation aid in oxidative phosphorylation, the last step in cellular respiration, which in turns aids the in the production of ATP.

Additionally, it is believed that photobiomodulation releases nitric oxide from the mitochondria. It is believed that nitric oxide prevents or reduces the production of ATP. Additionally, the release of nitric oxide has been clinically proven to reduce heart attacks and strokes, increase blood flow to the brain, reduce lactic acid build up in muscles and boost the immune system.

In other studies, photobiomodulation documented benefits include assisting in relief from seasonal affective disorder (SAD) and depression, and reducing insulin sensitively. Finally, it is believed that photobiomodulation aids in stopping the creation of free radicals.

Although the present disclosure has been described with reference to preferred embodiments, workers skilled in the art will recognize that changes may be made in form and detail without departing from the spirit and scope of the disclosure.

The invention claimed is:

1. A chamber for one or more persons to exercise, the chamber comprising:
   at least one emitting system configured to emit FIR energy;
   at least one panel comprising a plurality of natural stones, the at least one panel being secured in a vertical plane in front of one of the at least one emitting system configured to emit the FIR energy also installed in a vertical plane within the chamber and such that a portion of the FIR energy emitted is absorbed by at least some of the plurality of natural stones to heat the at least some of the plurality of natural stones which emit photons into the chamber, and a second portion of the FIR energy emitted passes through spaces between adjacent natural stones and into the chamber; and
   a control panel configured to control the duration of the FIR energy within the chamber wherein the chamber is sized to allow one or more persons to perform exercise or to sit,
   wherein an environment within the chamber is selectively controllable including a temperature to provide an environment different from ambient in which the one or more persons can exercise.

2. The chamber of claim 1 and further comprising an optically transparent or translucent door such that the exerciser is visible through the door.

3. The chamber of claim 1 and further comprising at least one light emitting source configured to emit visible light at a wavelength in the range of about 620 to 750 nm and wherein the controller is further configured to control the duration of a selected wavelength of the visible light emitted in the chamber.

4. The chamber of claim 1 and further comprising a seat within the chamber.

5. The chamber of claim 1, wherein one wall of the chamber includes a substantially open space configured for the exerciser to lean or brace against the open space while exercising.

6. The chamber of claim 1 and further comprising an access door in one of the walls of the chamber, wherein the access door is configured to open to provide access to electric sockets and to close to protect the electric sockets from the heat in the environment when not in use.

7. The chamber of claim 1 and further comprising a wireless internet enabled screen mounted on one of the walls, wherein the wireless internet enabled screen is configured to stream video from a source remote from the wireless internet enabled screen.

8. The chamber of claim 1 and further comprising:
a source of oxygen remote from the chamber, wherein the controller is configured to control the source of oxygen to enrich the oxygen concentration within the chamber.

9. The chamber of claim 1 and further comprising:
sources of moisture, carbon based materials and essential oils, wherein the controller is configured to control the sources of moisture, carbon based materials and essential oils independent of each other to modify the environment within the chamber.

10. A method of customizing an environment within in-a chamber for one or more persons to exercise, the method comprising:
providing at least one far infrared radiation (FIR) emitting system mounted within the chamber in a vertical plane and configured to emit FIR energy;
providing at least one panel securing a plurality of spaced apart natural stones within a framework of the at least one panel and the panel positioned in a vertical plane directly in front of at least one of the at least one FIR emitting system configured to emit the FIR energy when heated and wherein at least a portion of the FIR energy emitted heats the plurality of natural stones causing the natural stones to emit photons into the chamber and wherein at least a portion of the FIR energy emitted passes through one or more spaces between adjacent natural stones of the plurality of natural stones and into the chamber and wherein the at least one panel and the FIR emitting system are vertically installed within the chamber; and controlling the duration that the at least one FIR emitting system is energized, such that the environment is at a selected temperature such that the one or more persons can exercise in the environment within the chamber that is different from an ambient environment.

11. The method of claim 10 and further comprising:
providing at least one MIR emitter system mounted within the chamber and configured to emit MIR energy; and
controlling the duration that the at least one MIR emitter system is energized.

12. The method of claim 10 and further comprising:
providing a source of oxygen proximate the chamber; and
controlling a flow of oxygen into the chamber to enrich the oxygen content within the chamber.

13. The method of claim 10 and further comprising:
providing a source of moisture proximate the chamber; and
controlling a flow of the moisture into the chamber to increase the humidity within the chamber.

14. The method of claim 10 and further comprising:
providing a screen within the chamber; and
controlling visual content displayed on the screen.

15. The method of claim 14 and wherein control visual content on the screen comprises receiving the visual content from a cell phone remote from the screen.

16. The method of claim 10 and further comprising:
providing a source of essential oils proximate the chamber; and
controlling a flow of the essential oils into the chamber to provide aroma therapy within the chamber.

17. The method of claim 10 and further comprising:
providing a source of carbon based materials proximate the chamber; and
controlling a flow of the carbon based materials into the chamber to modify the environment within the chamber for the exerciser.

18. The method of claim 10 and further comprising:
providing a salt block within the chamber; and
heating the salt block to provide halotherapy within the chamber.

19. The method of claim 10, wherein the exercise comprises yoga, tai chi, active recovery, active rest disciplines, stretching, assisted stretching physical therapy manipulation and combinations thereof.

20. The method of claim 10, wherein the exercise comprises utilizing a treadmill, an elliptical machine, a stationary bicycle, a rowing machine, weights or resistance bands.

21. The method of claim 10 and further comprising providing at least one visible light emitting source positioned within the chamber and further controlling a wavelength and a duration of the at least one visible light emitting source when energized such that the environment is at a selected temperature and a selected color of visible light.

* * * * *